United States Patent [19]

van der Burg

[11] 4,002,632
[45] Jan. 11, 1977

[54] TETRACYCLIC PIPERIDINO DERIVATIVES

[75] Inventor: Willem Jacob van der Burg, Heesch, Netherlands

[73] Assignee: Akzona Incorporated, Asheville, N.C.

[22] Filed: Jan. 22, 1975

[21] Appl. No.: 543,199

[30] Foreign Application Priority Data

Jan. 31, 1974 Netherlands ............ 7401324

[52] U.S. Cl. .............. 260/290 H; 260/293.73; 260/293.79; 260/293.8; 260/294.8 A; 260/296 P; 260/297 F; 260/315; 260/329.3; 260/346.2 M; 260/470; 260/471 A; 260/473 G; 260/473 R; 424/263

[51] Int. Cl.² ............ C07D 221/18; C07D 471/22; C07D 491/22; C07D 495/22

[58] Field of Search ............ 260/290 H, 294.8 A, 260/296 P, 297 F

[56] References Cited

UNITED STATES PATENTS

| 3,479,356 | 11/1969 | Fouche et al. ............ 260/290 H |
| 3,860,606 | 1/1975 | van der Burg ............ 260/309.7 |

FOREIGN PATENTS OR APPLICATIONS

| 7,202,963 | 9/1973 | Netherlands ............ 260/309.7 |

OTHER PUBLICATIONS

Blattner et al., I, Chem. Abst., 1970, vol. 73, No. 45488p.
Blattner et al., II, Chem. Abst., 1970, vol. 73, No. 45491j.
Blattner et al., III, Chem. Abst., 1972, vol. 76, No. 72494f.
Blattner et al., IV, Chem. Abst., 1972, vol. 76, No. 140762u.
Blattner et al., V, Chem. Abst., 1972, vol. 77, Nos. 126600d, 126601e & 1266303g.
Organon, Chem. Abst., 1969, vol. 70, No. 115192b.

*Primary Examiner*—Natalie Trousoe
*Attorney, Agent, or Firm*—Francis W. Young; Philip M. Pippenger; Hugo E. Weisberger

[57] ABSTRACT

The invention relates to antidepressive biologically active tetracyclic piperidino derivatives of the general formula:

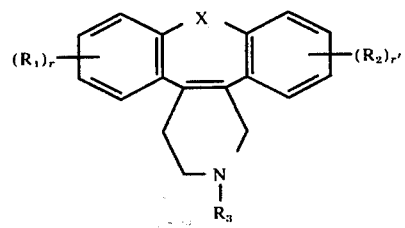

I as well as the pharmaceutically acceptable salts and nitrogen oxides ($N_2$) thereof, in which:

$R_1$ and $R_2$ represent hydroxy, halogen, alkyl (1–6 C), alkoxy (1–6 C), alkylthio (1–6 C) or trifluoromethyl, $R_3$ stands for hydrogen, alkyl (1–6 C) or aralkyl (7–10 C), $r$ and $r'$ stand for the number 0, 1 or 2, X represents oxygen, sulphur, the group $>NR_4$ or methylene and $R_4$ stands for hydrogen or alkyl (1–4 C).

5 Claims, 1 Drawing Figure

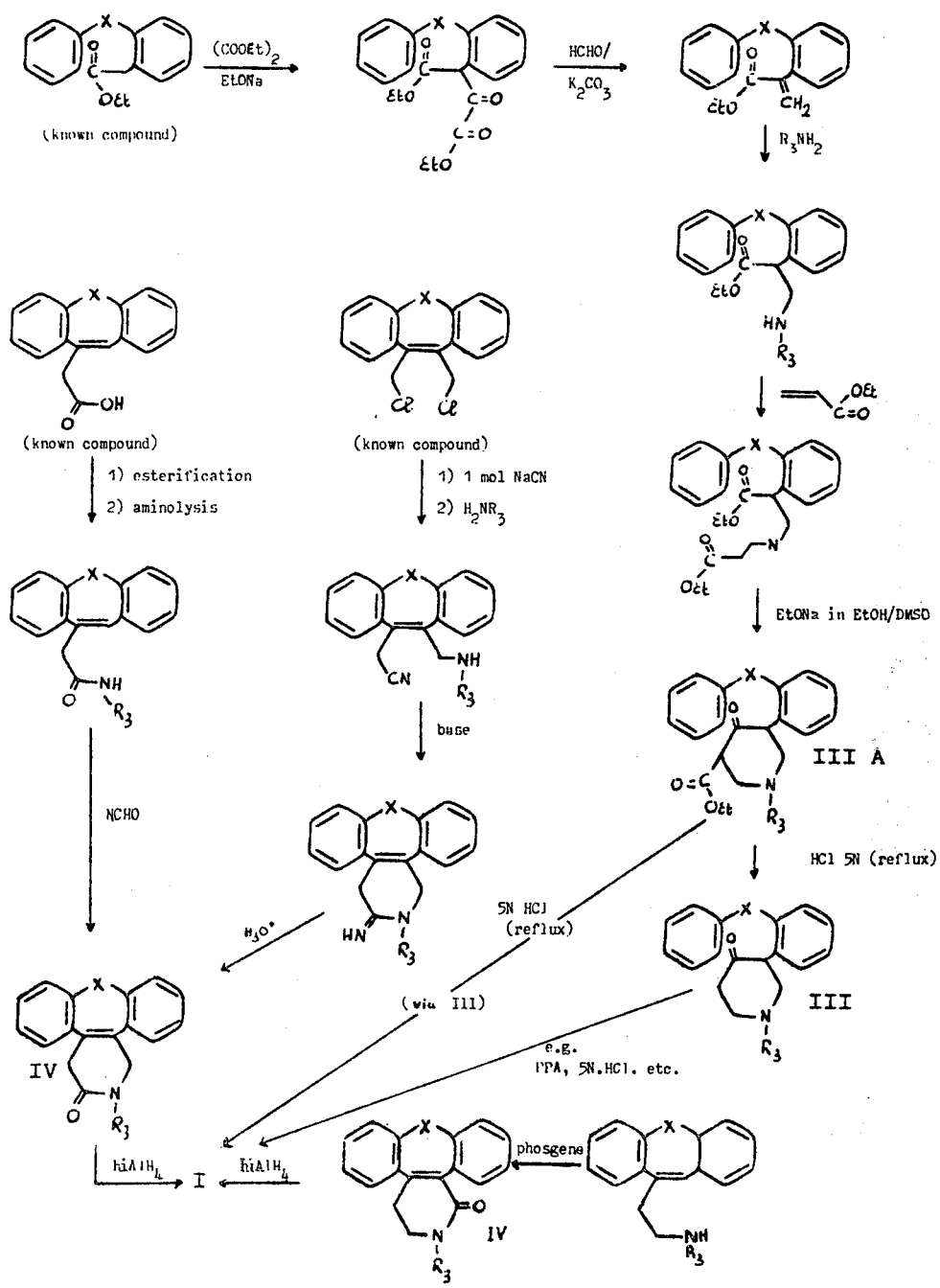

TETRACYCLIC PIPERIDINO DERIVATIVES

The invention relates to novel biologically active tetracyclic piperidino derivatives, to processes for preparing these compounds and to pharmaceutical preparations containing these novel tetracyclic compounds as the active constituent.

It was found that compounds of the general formula:

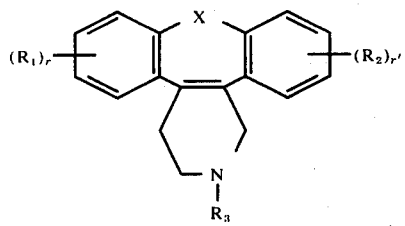

as well as the pharmaceutically acceptable salts and nitrogen oxides ($N_2$) thereof, in which:

$R_1$ and $R_2$ represent hydroxy, halogen, alkyl (1–6 C), alkoxy (1–6 C), alkylthio (1–6 C) or trifluoromethyl, $R_3$ stands for hydrogen, alkyl (1–6 C) or aralkyl (7–10 C), $r$, and $r'$ stand for the number 0, 1 or 2, X represents oxygen, sulphur, the group >$NR_4$ or methylene and $R_4$ stands for hydrogen or alkyl (1–4 C), have very valuable biological properties. More particularly the compounds according to formula I possess anti-depressive activity and are thus useful in the treatment of individuals suffering from depression.

Compounds are known which differ from the present compounds according to the invention in that they possess a pyrrolidino-ring instead of a piperidino ring. These known pyrrolidino-derivatives inhibit the activity of the central nervous system. On the basis of various biological tests it was concluded that these known pyrrolidino derivatives are particularly useful in treating conditions of stress and agitation or in other words that the compounds can be used as sedatives or tranquillizers.

Surprisingly it was found that besides moderate sedative properties the present compounds are showing a pronounced antagonizing effect in the reserpine-antagonism and reserpine reversal test, which is characteristic for anti-depressive activity, whereas the known pyrrolidino derivatives show a potent facilitating effect in these tests. This combination of antidepressant and sedative properties renders the present compounds particularly useful in treating depressed patients with suicidal tendencies.

Moreover, the present compounds exhibit an improved resorption in respect of the known pyrrolidino-compounds, owing to which lower oral dosages will suffice.

The compounds according to the invention can be prepared by any method commonly used for the preparation of this type of compounds.

A very convenient synthesis for the preparation of the present compounds I consists of a condensation of a compound with the general formula II:

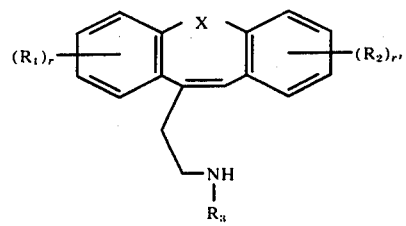

or a salt thereof, in which X, $R_1$, $R_2$, $R_3$, $r$ and $r'$ have the meaning mentioned above, with formaldehyde or paraformaldehyde in a suitable solvent. This reaction is preferably carried out at the boiling-temperature of the solvent, but also a lower reaction-temperature can be used.

This condensation reaction can further be promoted by adding a suitable catalyst, preferably acids such as phosphoric acid, polyphosphoric acid, sulphuric acid, hydrochloric acid, etc., whereby the acid may simultaneously be used as solvent.

The starting substances II are known compounds.

Another method in preparing the present compounds consists of a cyclisation of a starting compound of the general formula III:

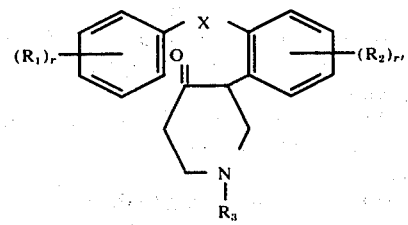

or a salt thereof, in which $R_1$, $R_2$, $R_3$, X, $r$ and $r'$ have the meaning mentioned above. This cyclisation is carried out at a raised temperature, for instance at the boiling temperature of the solvent used. Like described for the first-mentioned synthesis, this cyclisation is also promoted by adding a catalyst in order to stimulate the dehydration during the cyclisation. Catalysts which are commonly used in this connection are for instance, hydrochloric acid, sulphuric acid, p.toluenesulphonic acid, phosphoric oxide, phosphoroxychloride, phosphoric acid, polyphosphoric acid, aluminiumchloride, borontrifluoride, tintetrachloride, zinc chloride, etc.

The starting substances of the general formula III are novel compounds which can be prepared by any method commonly used for this type of compounds, for example in the manner as indicated in the attached flow sheet. Otherwise it is not absolutely necessary to isolate the starting substance III. As appears from the flow sheet, the compound III A can also be converted directly into a compound according to the invention without isolating the intermediate compound III.

Another synthesis of the present compounds consists of the reduction of one or more oxo groups of a compound of the general formula IV:

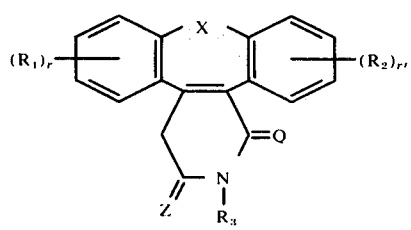

in which X, $R_1$, $R_2$, $R_3$, $r$ and $r'$ have the meaning mentioned above and Z and Q represent hydrogen (2H) or oxygen, on the understanding that at least one of the substituents Z and Q is oxygen, into the corresponding —$CH_2$—group. This reaction is performed by a method commonly used for this type of compounds.

Suitable reducing agents in this connection are for example di-isobutylaluminiumhydride, lithiumboronhydride, sodium-trimethoxyboronhydride and preferably diboran or lithiumaluminiumhydride.

The starting substances IV are novel compounds. They can be prepared by a method commonly used for this type of compounds e.g. in the manner as indicated in the attached flow sheet. They are the preferred intermediate products in preparing the compounds according to the invention.

The alkyl group mentioned in the definition of $R_1$, $R_2$ and $R_3$ means a branched or unbranched alkyl group with 1–6 C atoms, e.g. methyl, ethyl, propyl, isopropyl, butyl, isobutyl, sec. butyl, tert. butyl, pentyl, isopentyl or neopentyl. The same definition holds for the alkyl group of the alkoxy- and alkylthio group in $R_1$ and $R_2$.

The aralkyl group as meant in the definition of $R_3$ is preferably a phenylalkyl group with 7 to 10 carbon atoms, such as benzyl, phenylethyl, phenylpropyl or 1-methylphenylethyl.

With salts of the compounds of the general formula I are meant the acid addition salts and quaternary ammonium salts.

The acid addition salts according to the invention are prepared in the usual manner by reacting the free base I with a pharmaceutically acceptable acid. Suitable acids in this connection are: hydrochloric acid, hydrobromic acid or hydroiodic acid, phosphoric acid, acetic acid, propionic acid, glycollic acid, maleic acid, malonic acid, succinic acid, tartaric acid, citric acid, ascorbic acid, salicylic acid or benzoic acid.

The quaternary ammonium compounds, particularly the lower (1–4 C) alkyl quaternary ammonium compounds, are obtained by reacting the compounds of the general formula I with an alkylhalogenide, for instance methyl iodide or methyl bromide.

The nitrogen oxides of the compounds according to the general formula I are obtained by oxidation of the free base I with hydrogenperoxyde or a peracid.

It is, of course, possible to introduce or to modify the substituents $R_1$ and/or $R_2$ also after the afore-mentioned condensation reactions.

Thus a hydroxyl group present can be converted into an alkoxy group, an amino group into halogen, a methoxy group into a hydroxy group etc. Preferably, however, these substituents ($R_1$, $R_2$) are already present in the starting products II, III or IV.

Although the desired substituent at the nitrogen atom of position 2 of the molecule I is preferably already present in the starting products II, III or IV, this substituent ($R_3$ is other than hydrogen) can be introduced very well after the afore-said condensation reactions.

Thus, the unsubstituted amines of the general formula I ($R_3 = H$) can be alkylated in the usual way, for instance by reaction with an alkyl- or aralkyl-halogenide. The said alkylation is, however, preferably carried out by acylating the nitrogen atom in question for example with an acid chloride or anhydride and after that reducing the keto group of the N-acyl derivative obtained. A methyl group at the nitrogen atom ($R_3 = CH_3$) is preferably introduced by means of the Eschweiler-Clarke procedure (heating with a mixture of formaldehyde and formic acid) or by the reaction with formaldehyde and sodiumcyanoborohydride in a suitable solvent, such as acetonitril.

The substituted amines of formula I ($R_3 \neq H$) can moreover be converted into the corresponding unsubstituted amine of formula I ($R_3 = H$). A very convenient method to that effect consists of the reaction of the alkyl- or aralkyl substituted amine I with a chloroformic acid ester followed by hydrolysis of the compound obtained.

The antidepressive compounds according to the invention can be administered orally, rectally as well as parenterally, preferably in a daily dosage of from 0.01 to 10 mg per kg body weight.

Together with suitable auxiliaries the compounds I can be compressed into solid dosage units such as pills, tablets, suppositories or coated tablets. They may also be processed into capsules in the usual manner. With the aid of suitable liquids the compounds I may be applied as injection preparations in the form of (sterile) solutions, emulsions or suspensions.

Preferred compounds according to the invention are those compounds in which (whether or not in combination): X stands for oxygen, the group >$NCH_3$ or methylene; $R_3$ for methyl; $r$ and $r'$ for the number 0 or 1 and $R_1$ and/or $R_2$ for methyl, preferably at position 6 and/or 12 of the molecule.

In the examples the following nomenclature and numbering has been used:

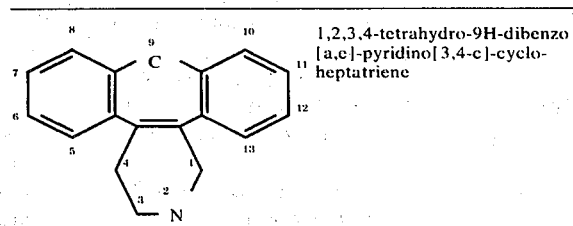

1,2,3,4-tetrahydro-9H-dibenzo[a,e]-pyridino[3,4-c]-cycloheptatriene

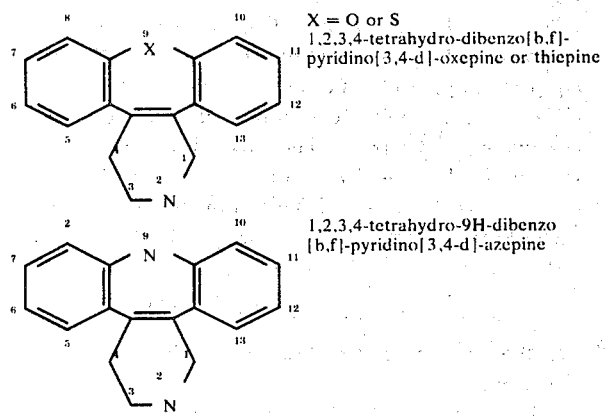

X = O or S
1,2,3,4-tetrahydro-dibenzo[b,f]-pyridino[3,4-d]-oxepine or thiepine 1,2,3,4-tetrahydro-9H-dibenzo[b,f]-pyridino[3,4-d]-azepine

EXAMPLE I

Preparation of 2(N)-methyl-1,2,3,4-tetrahydro-9H-dibenzo[a,e]-pyridino[3,4-c]-cycloheptatriene maleate 23.5 g of 3-(2-benzyl-phenyl)-5-carbethoxy-1-methylpiperidon-4 are added to 425 ml of 5 N hydrochloric acid. The mixture is refluxed for 2 hours. After being cooled down the reaction mixture is poured on ice after which the mixture is made alkaline with a concentrated solution of sodium hydroxide. The mixture is extracted with benzene and the benzene extract then washed with water. The benzene solution is extracted with 2 N hydrochloric acid. The hydrochloric acid extract is then made alkaline with a solution of sodium hydroxide. Extraction into ether and washing, drying and evaporating the ether-extract yields 13.6 g of a mixture of 3-(2-benzyl-phenyl)-1-methyl-piperidon-4 and 2(N)-methyl-1,2,3,4-tetrahydro-9H-dibenzo[a,e]-pyridino [3,4-c]-cycloheptatriene.

This mixture is added to 100 g of polyphosphoric acid and while stirring heated at 100° C for 1 hour.

The reaction mixture is poured on ice and made alkaline. Extraction into ether and washing the extract with water, drying on anhydrous magnesium sulphate and evaporation yields 9.6 g of 2(N)-methyl-1,2,3,4-tetrahydro-9H-dibenzo [a,e]-pyridino[3,4-c]-cycloheptatriene. The brownish colour is removed by washing with ether.

The maleic acid salt is obtained by treating the free base obtained with an alcoholic solution of maleic acid. Yield: 9.8 g of the maleate; melting point 160°–162° C.

A treatment of the free base obtained with hydrogenperoxide yields the corresponding nitrogen oxide and with methyliodide the corresponding iodomethylate (m.p. 245°–250° C).

EXAMPLE II

2(N)-methyl-6-methoxy-1,2,3,4-tetrahydro-9H-dibenzo[a,e]-pyridino[3,4-c]-cycloheptatriene In the same manner as described in Example I 28 g 3-[2-(p-methoxybenzyl)-phenyl]-5-carbethoxy-1-methyl-piperidon-4 is converted into 13.5 g of 2(N)-methyl-6-methoxy-1,2,3,4-tetrahydro-9H-dibenzo[a,e]-piridino [3,4-c]-cycloheptatriene, obtained as a light yellow coloured oil; Rf in methanol = 0.4 (on $SiO_2$).

EXAMPLE III

2(N)-methyl-1,2,3,4-tetrahydro-dibenzo[b,f]-pyridino[3,4-d]-oxepine maleate 25 g of 3-2-phenoxy-phenyl)-5-carbethoxy-1-methyl-piperidon-4 are added to 500 ml of 4 N hydrochloric acid after which the mixture is refluxed for 3 hours. The mixture is then extracted in the same manner as described in Example I, yielding a mixture of the endproduct and the 5-descarboxy starting product. This mixture is heated at 95°–100° C for 1.5 hour in 130 g of polyphosphoric acid, while stirring. The endproduct is isolated in the same way as described in Example I. Yield: 11.5 g of the maleate; melting point: 136°–140° C.

EXAMPLE IV

In a similar manner as described in Example III are prepared:
2(N), 12-dimethyl-1,2,3,4-tetrahydro-dibenzo[b,f]-pyridino [3,4-d]-oxepine maleate, melting point: 156°–160° C;
2(N)-methyl-6-methoxy-1,2,3,4-tetrahydro-dibenzo[b,f]-pyridino[3,4-d]-oxepine fumarate, melting point: 200°–203° C.

EXAMPLE V 2N-methyl-1,2,3,4-tetrahydro-dibenzo[b,f]-pyridino[3,4-d]-thiepine maleate 2.5 g of 3-(2-phenylthio-phenyl)-1-methyl-piperidon-4 are added to 30 g of polyphosphoric acid, after which the mixture is heated for 1 hour at about 100° C. Then the reaction mixture is poured on ice and made alkaline with concentrated sodium hydroxide. Extraction of the mixture into ether and washing the ether extract with water, drying on magnesium sulphate and evaporation yields 1.6 g of 2(N)-methyl-1,2,3,4-tetrahydro-dibenzo[b,f]-pyridino [3,4-d]-thiepine (oil).

The oily product is then treated with an alcoholic solution of maleic acid yielding the maleate salt in crystalline form. Melting point: 159°–161° C.

In a corresponding manner are prepared:
2(N),9(N')-dimethyl-1,2,3,4-tetrahydro-dibenzo[b,f]-pyridino [3,4-d]-azepine maleate;
2(N),6-dimethyl-1,2,3,4-tetrahydro-9H-dibenzo[a,e]-pyridino [3,4-c]-cycloheptatriene maleate and hydrochloric acid salt;

2(N)-methyl-6-chloro-1,2,3,4-tetrahydro-9H-dibenzo[a,e]-pyridino [3,4-c]-cycloheptatriene;
2(N)-propyl-1,2,3,4-tetrahydro-9H-dibenzo[a,e]-pyridino [3,4-c]-cycloheptatriene;
2(N)-phenylethyl-1,2,3,4-tetrahydro-9H-dibenzo[a,e]-pyridino[3,4-c]-cycloheptatriene;
2(N)-benzyl-9(N)-methyl-1,2,3,4-tetrahydro-dibenzo[b,f]-pyridino [3,4-d]-azepine;
1,2,3,4-tetrahydro-9H-dibenzo[a,c]-pyridino[3,4-c]-cycloheptatriene;
9(N)-methyl-1,2,3,4-tetrahydro-dibenzo[b,f]-pyridino[3,4-d]-azepine;
2(N)-methyl-12-trifluoro-1,2,3,4-tetrahydro-dibenzo[b,f]-pyridino [3,4-d]-thiepine.

EXAMPLE VI

2(N),6-dimethyl-1,2,3,4-tetrahydro-9H-dibenzo[a,e]-pyridino [3,4-c]-cycloheptatriene.maleate 18 g of 3-methyl-5-methylaminoethyl-dibenzo[a,e]-cycloheptatriene are added to a mixture of 360 ml of 2N hydrochloride acid and 40 ml of ethanol to which 35 ml of a 40 % formaldehyde solution in water has been added. The mixture is refluxed for 3 hours. The alcohol is then evaporated in vacuo and the remaining liquid is made alkaline. After an extraction of the reaction mixture with an ether-benzene mixture (1:1) and washing of the extract with water, drying on anhydrous magnesium sulphate and evaporation, 16.5 g of the crude product is obtained. With an alcoholic solution of maleic acid the crude product obtained is converted into 14.8 g of the maleate. Melting point: 177°–178° C.

EXAMPLE VII

In a corresponding manner as described in Example VI, the following compounds are prepared on the understanding that when preparing the compounds with X = O, S or $NR_4$, the reaction mixture is refluxed for 10 hours and the final product (free base) is purified by means of column-chromatography.

2(N)-methyl-6-chloro-1,2,3,4-tetrahydro-[9H-dibenzo[a,e]-pyridino[3,4-c]-cycloheptatriene;
2(N)-methyl-6-methoxy-1,2,3,4-tetrahydro-dibenzo[b,f]-pyridino[3,4-d]-oxepine.fumarate;
2(N),12-dimethyl-1,2,3,4-tetrahydro-dibenzo[b,f]-pyridino [3,4-d]-oxepine.maleate;
9(N)-methyl-1,2,3,4-tetrahydro-dibenzo[b,f]-pyridino[3,4-d]-azepine;
2(N),9(N)-dimethyl-1,2,3,4-tetrahydro-dibenzo[b,f]-pyridino [3,4-d]-azepine.maleate;
2(N)-benzyl,9(N)-methyl-1,2,3,4-tetrahydro-dibenzo[b,f]-pyridino[3,4-d]-azepine;
2(N)-propyl-1,2,3,4-tetrahydro-9H-dibenzo[a,e]-pyridino [3,4-c]-cycloheptatriene;
2(N)-methyl-1,2,3,4-tetrahydro-dibenzo[b,f]-pyridino[3,4-d]-thiepine.maleate;
2(N)-methyl-1,2,3,4-tetrahydro-dibenzo[b,f]-pyridino[3,4-d]- oxepine.maleate;
2(N)-6,7-trimethyl-1,2,3,4-tetrahydro-dibenzo[b,f]-pyridino [3,4-d]-oxepine.

EXAMPLE VIII

Preparation of
2(N)-methyl-1,2,3,4-tetrahydro-dibenzo[b,f]-pyridino[3,4-d]-thiepine.maleate 10 g of 2(N)-methyl-3oxo-1,2,3,4-tetrahydro-dibenzo [b,f]-pyridino[3,4-d]-thiepine are added to a suspension of 20 g of lithiumaluminiumhydride in 150 ml of tetrahydrofurane. While stirring the mixture is refluxed for 1 hour. The reaction mixture is cooled down to 0° C after which 40 ml of water are added dropwise. The mixture is then stirred for another hour at room temperature and filtered. The filtrate is evaporated in vacuo and the residue obtained purified by columnchromatography. The purified residue is treated with an alcoholic solution of maleic acid yielding 7.2 g of 2(N)-methyl-1,2,3,4-tetrahydro-dibenzo[b,f]-pyridino[3,4-d]-thiepine.maleate. Melting point: 161°–162° C.

EXAMPLE IX

In the same manner as described in Example VIII are prepared:

2(N),6-dimethyl-1,2,3,4-tetrahydro-9H-dibenzo[a,e]-pyridino [3,4-c]-cycloheptatriene.maleate from the corresponding 3-oxo-compound;
2(N),9(N)-dimethyl-1,2,3,4-tetrahydro-dibenzo[b,f]-pyridino [3,4-d]-azepine.maleate from the corresponding 1- and 3-oxo compound;
2(N)-methyl-6-methoxy-1,2,3,4-tetrahydro-dibenzo[b,f]-pyridino [3,4-d]-oxepine.fumarate, from the corresponding 3-oxo-compound;
2(N)-methyl-12-trifluoro-1,2,3,4-tetrahydro-dibenzo[b,f]-pyridino [3,4-d]-thiepine, from the corresponding 3-oxo-compound;
2(N)-propyl-1,2,3,4-tetrahydro-9H-dibenzo[a,e]-pyridino [3,4-c]-cycloheptatriene from the corresponding 3-oxo-compound;
9(N)-methyl-1,2,3,4-tetrahydro-dibenzo[b,f]-pyridino[3,4-d]-azepine, from the corresponding 1-oxo compound;
2(N)-methyl-6-hydroxy-1,2,3,4-tetrahydro-dibenzo[b,f]-pyridino [3,4-d]-oxepine from the 3-oxo compound.

I claim:
1. A compound of the formula:

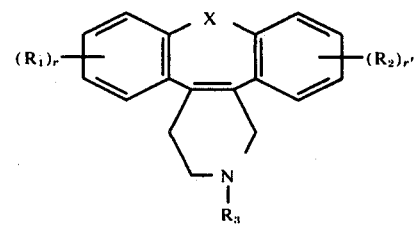

or a pharmaceutically acceptable salt or nitrogen oxide thereof, in which $R_1$ and $R_2$ represent hydroxy, halogen, alkyl (1–6 C), alkoxy (1–6 C), alkylthio (1–6 C) or trifluoromethyl, $R_3$ stands for hydrogen, alkyl (1–6 C) or aralkyl (7–10 C), X represents oxygen, sulphur, the group >$NR_4$ or methylene ($CH_2$), $R_4$ stands for hydrogen or alkyl (1–4 C) and $r$ and $r'$ represent the number 0, 1 or 2.

2. A compound according to claim 1 of the formula:

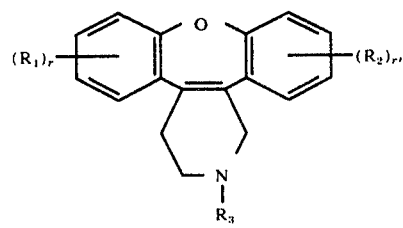

or a pharmaceutically acceptable salt thereof, in which $R_1$, $R_2$, $R_3$, $r$ and $r'$ have the meaning as described in claim 1.

3. A compound according to claim 1 of the formula:

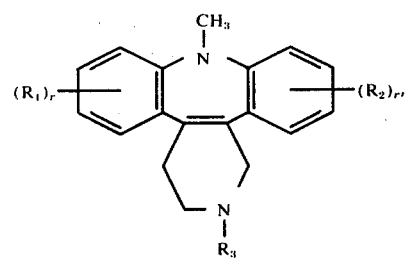

or a pharmaceutically acceptable salt thereof in which $R_1$, $R_2$, $R_3$, $r$ and $r'$ have the meaning as described in claim 1.

4. A compound according to claim 1 of the formula:

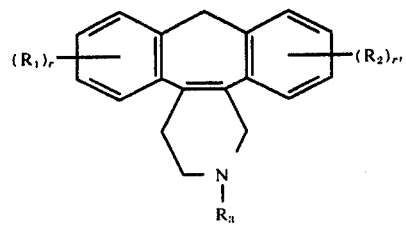

or a pharmaceutically acceptable salt thereof, in which $R_1$, $R_2$, $R_3$, $r$ and $r'$ have the meaning as described in claim 1.

5. A compound according to claim 1 of the formula:

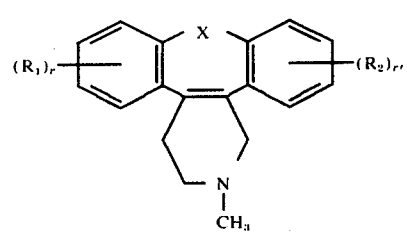

or a pharmaceutically acceptable salt thereof in which X stands for methylene, or oxygen, $r$ and $r'$ for the number 0 or 1 and $R_1$ and $R_2$ for methyl.

* * * * *